(12) United States Patent  (10) Patent No.: US 8,506,549 B2
Breuer-Thal et al.  (45) Date of Patent: Aug. 13, 2013

(54) MULTI-PURPOSE CONNECTOR FOR ENTERAL APPLICATION

(75) Inventors: Barbara Breuer-Thal, Hattersheim (DE); Marcel Oster, Moenchengladbach (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 574 days.

(21) Appl. No.: 12/310,394

(22) PCT Filed: Aug. 28, 2007

(86) PCT No.: PCT/EP2007/007519
§ 371 (c)(1),
(2), (4) Date: Feb. 24, 2009

(87) PCT Pub. No.: WO2008/028582
PCT Pub. Date: Mar. 13, 2008

(65) Prior Publication Data
US 2010/0022986 A1  Jan. 28, 2010

(30) Foreign Application Priority Data
Sep. 4, 2006 (DE) .......................... 10 2006 041 414

(51) Int. Cl.
*A61M 39/10* (2006.01)
*A61M 39/14* (2006.01)
*A61J 1/20* (2006.01)

(52) U.S. Cl.
USPC .............. 604/411; 604/414; 604/86; 604/533

(58) Field of Classification Search
USPC ......... 604/258, 411, 412, 414, 416, 533–536, 604/81, 86; 215/250, 319
See application file for complete search history.

(56) References Cited

U.S. PATENT DOCUMENTS

| | | | |
|---|---|---|---|
| 3,019,932 A | 2/1962 | Singiser | |
| 4,469,335 A * | 9/1984 | Moore | 277/648 |
| 4,969,565 A | 11/1990 | Justal et al. | |
| 5,437,655 A * | 8/1995 | Bartholomew | 604/406 |
| 5,738,663 A * | 4/1998 | Lopez | 604/249 |
| 6,874,522 B2 * | 4/2005 | Anderson et al. | 137/68.3 |
| 6,875,204 B1 * | 4/2005 | Hopkins et al. | 604/414 |
| 7,611,502 B2 * | 11/2009 | Daly | 604/414 |
| 2005/0033267 A1 * | 2/2005 | Decaria | 604/533 |
| 2007/0112323 A1 * | 5/2007 | Daly | 604/411 |
| 2007/0129705 A1 * | 6/2007 | Trombley et al. | 604/523 |

FOREIGN PATENT DOCUMENTS

| | | | |
|---|---|---|---|
| EP | 0 355 795 A1 | 2/1990 | |
| EP | 0 711 538 B1 | 5/1996 | |
| EP | 0711538 | * 5/1996 | |

* cited by examiner

*Primary Examiner* — Philip R Wiest
*Assistant Examiner* — Benjamin Klein
(74) *Attorney, Agent, or Firm* — Jacobson Holman PLLC

(57) ABSTRACT

A multipurpose connector made in two pieces and having three distal connectors and two proximal connectors arranged concentrically in one another and coaxially to one another and made differently and having a venting passage. The multipurpose connector is used in gravity-assisted and pump-assisted enteral feeding and serves for the connection of transfer systems to storage containers, in particular to nutrient and balancing liquid containers having differently designed openings. Also provided is a set for enteral application including a transfer system and the multipurpose connector and the use of the multipurpose connector or of the set.

22 Claims, 6 Drawing Sheets

Fig. 3
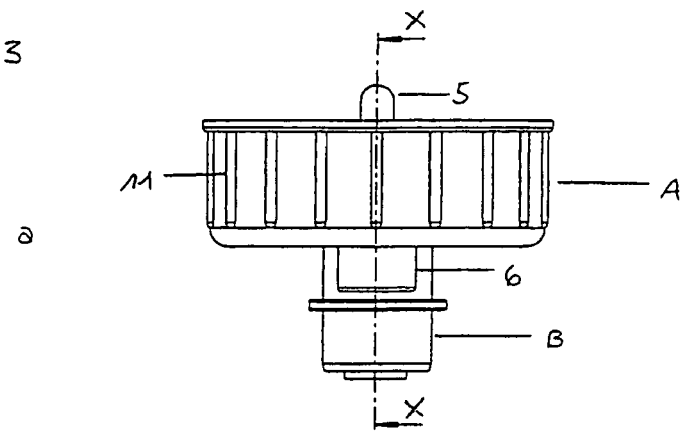
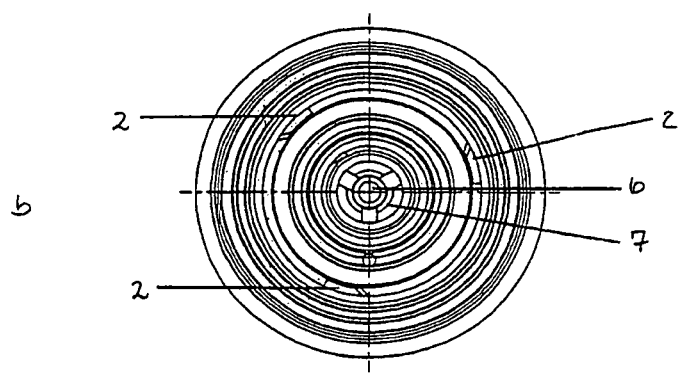
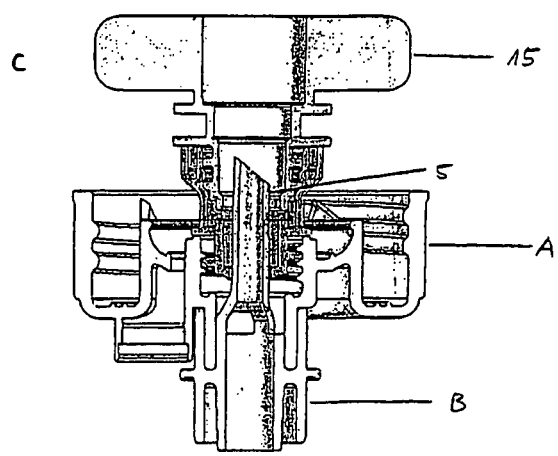

Fig. 5
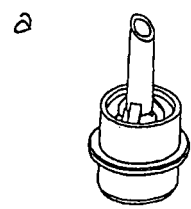
a
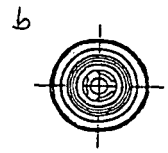
b
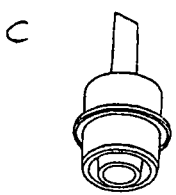
c
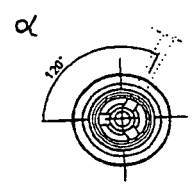
α
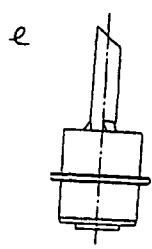
e
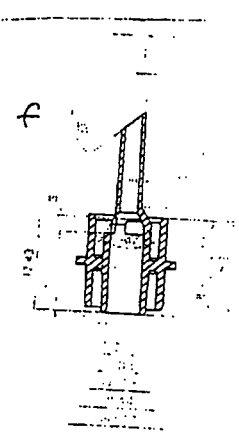
f

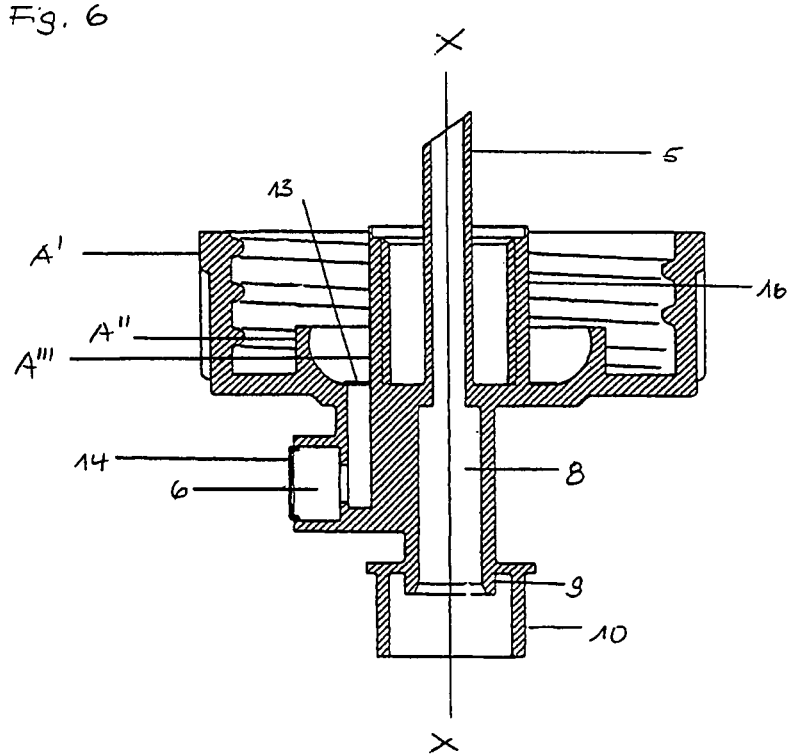

MULTI-PURPOSE CONNECTOR FOR ENTERAL APPLICATION

This is a national stage of PCT/EP2007/007519 filed Aug. 28, 2007 and published in German, which has a priority of German no. 10 2006 041 414.4 filed Sep. 4, 2006, hereby incorporated by reference.

BACKGROUND OF THE INVENTION

1. Field of the Invention

The invention relates to a multipurpose connector for the connection of enteral transfer systems to storage containers, in particular to nutrient and balancing liquid containers. The multipurpose connector includes three different distal connectors disposed concentrically in one another and coaxially to one another for the connection of enteral transfer systems to storage containers having differently designed openings. The multipurpose connector can be used in enteral feeding both in pump-assisted systems and in gravity controlled systems. The invention also relates to a set having at least one such multipurpose connector. The invention furthermore relates to the use of the multipurpose connector or of a set having at least one such multipurpose connector.

2. Description of the Related Art

If a patient is no longer able to ingest or swallow food due to a disease, the most important nutrients can be supplied to him in liquid form via a feed probe.

The feed probe is either guided temporarily through the nose into the stomach or into the small intestine or it is permanently placed in the stomach or small intestine via a small puncture site through the abdominal wall. A transfer system connects the feed probe to the nutrient and balancing liquid container.

The transfer system comprises a tube with or without a drip chamber, a distal connector for connection to the enteral storage container and a proximal connector to the feed probe.

The enteral nutrient solution or balancing liquid is stored in containers, flasks or bags whose openings are admittedly normed or at least standardized, but which can be of different designs. The following are common inter alia: wide-mouth containers, for example containers or bottles made of glass or plastic with wide-mouth threads and additional aluminum or plastic protective foils, furthermore narrow-mouth containers such as crown cap bottles with a mouthpiece in accordance with DIN 6094 made of glass or hard plastic, and flexible containers such as pre-filled plastic bags with a puncture port.

The differently shaped storage container openings also require different, respectively adapted connectors for connection to the transfer system. The provision of different connectors adapted to the respective storage container type, however, increases the costs and moreover results in an increased handling effort such as the necessity of the laborious location of a suitable connector, of storage and of changing the connector during the application.

An adapter for the connection of enteral transfer systems is known from EP 0 355 795. The adapter is made of plastic and has two caps arranged coaxially to one another and having different opening diameters. However, the integration of a spike is lacking so that an additional connector with a transfer system is necessary for connection to the primary package containers made as bags or plastic containers with a port connector used in more than 50% of cases in enteral applications. The positioning of the vent valve at the inner side of the connector or in the interior of the nutrition and balancing liquid container is furthermore disadvantageous since blockages and a subsequent stop of conveying flow can occur.

A universal connector is known from U.S. Pat. No. 6,875,204 to which containers having three different opening diameters can be connected, with a spike representing one of the connection possibilities. A vent opening is, however, lacking in this known connector so that it is not suitable for use on rigid containers. The connector can furthermore not be directly connected to a transfer system, but can only be screwed into a wide-mouth bottle system.

A universal bottle closure is known from EP 0 711 538 having two differently sized coaxially arranged caps. The caps are made of different materials. The missing spike, on the one hand, and the riser tube integrated for the venting, on the other hand, are disadvantageous here. The latter makes it necessary that test liquid still remains in the container after the application.

SUMMARY OF THE INVENTION

It is therefore the object of the invention to provide a multipurpose connector for the connection of enteral transfer systems to storage containers having differently designed openings, said multipurpose connector having a variety of possibilities of use.

This object is satisfied by a multipurpose connector that includes three different distal connectors disposed concentrically in one another and coaxially to one another for the connection of enteral transfer systems to storage containers having differently designed openings. In addition, two further connectors are located at the oppositely disposed proximal side of the distal connectors for the storage containers, in particular for nutrition and balancing liquid containers.

The multipurpose connector in accordance with the invention has three different distal connectors and two different proximal connectors. All connectors are disposed concentrically in one another and coaxially to one another. An outer, a middle and an inner connector, which are each of different design, are located at the side remote from the patient, i.e. the distal side. Wide-mouth containers and narrow-mouth containers made of glass or plastic or also flexible storage containers with puncture ports can be connected in this manner. The advantages of a very cost-effective manufacture result on the basis of the product portfolio streamlined by the unification of different storage container variants and the thereby arising reduction in material and installation effort. Further advantages of the connector in accordance with the invention for the user can be found in the simplified handling and the less complex storage. The different storage containers and/or nutrient containers can also be used alternatingly, for example, without the connector simultaneously having to be changed.

Two further connectors, likewise disposed concentrically in one another and coaxially to one another, are located on the oppositely disposed side facing the patient, i.e. the proximal side, for direct assembly with a drip chamber or a tube.

Advantageous embodiments are the subject of the dependent claims.

The multipurpose connector is a two-piece injection molded part made of plastic and so cost-effective in manufacture. A part piece in this respect comprises the outer part, the middle part and a part of the inner distal connector and the two proximal connectors. Both part pieces are plugged into one another in production and latch in so doing. The possibility is advantageous in two-part manufacture of being able to use different material types or degrees of material hardness. It is, however, also possible to manufacture the multipurpose connector in one piece.

In an embodiment of the invention, the outer distal connector is provided with a screw thread, the middle distal connector is made as a snap connection and the inner distal connector is made as a guide with a thread and a central spike. The central spike has lateral material cut-outs which prevent the formation of residual liquid.

Wide-mouth containers, for example bottles having a wide-mouth thread, can be connected to the outer connector and narrow-mouth containers such as crown cap bottles can be connected to the middle connector. The inner connector is suitable for flexible containers, for example plastic bags having a puncture port. A confusion with intravenous spikes is precluded by the use of the spike in combination with a connector. In addition, the connector is not screwed onto a spike system as previously usual, but is rather advantageously connected directly to the drip chamber or to the transfer system tube, which saves additional material and assembly costs.

In a further embodiment, the multipurpose connector in accordance with the invention has a deaeration system. For this purpose, a venting passage is provided which preferably opens into the central distal connector and whose inner opening terminates flush with the base of the middle connector. A formation of residual liquid such as takes place in the universal bottle closure known from EP 0 711 538 due to the presence of a riser tube projecting beyond the base of the connector is thereby avoided.

The outer venting passage opening into which an assembly having a bacteria-tight filter and a venting valve can be inserted is located in the outer region of the connector. This positioning in the outer region prevents a blockage and thus an interruption of the nutrition conveying. The nutrient conveying is also promoted by the design which only permits smaller contact surfaces between the application medium and the connector.

The invention furthermore relates to a set for the connection of nutrient and balancing liquid connectors to a feed probe having at least one multipurpose connector for enteral application. The set includes a transfer system and the multipurpose connector in accordance with the invention and which allows the connection of storage containers having differently designed openings to the feed probe of a patient.

Furthermore, the use of a multipurpose connector or of a set for the connection of enteral transfer systems to nutrient and balancing liquid containers having differently designed openings is the subject of the invention.

In a further development of the invention, the connector can comprise different suitable materials familiar to the skilled person. In a special embodiment, the first part piece of the connector is transparent. This makes the spike visible and facilitates the puncturing process for the user.

The multipurpose connector can be provided with different connection possibilities familiar to the skilled person such as screw connections, snap connections or plug-in connections.

The set in accordance with the invention for the connection of nutrient and balancing liquid containers having differently designed openings to a feed probe comprises a transfer system and the multipurpose connector in accordance with the invention. The set can include a drip chamber; the connection between the transfer system and one of the two proximal connectors of the multipurpose connector can, however, also only be established via a tube.

BRIEF DESCRIPTION OF THE DRAWINGS

Further details of the invention will be described in more detail with reference to an embodiment shown in the drawings. There are shown:

FIGS. 3a-c different views of the multipurpose connector in accordance with the invention shown in FIGS. 1 and 2;

FIGS. 5a-f different views of the second part piece of the multipurpose connector in accordance with the invention; and FIG. 6 a one-dimensional longitudinal section through an alternative one-piece embodiment of a multipurpose connector in accordance with the invention.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
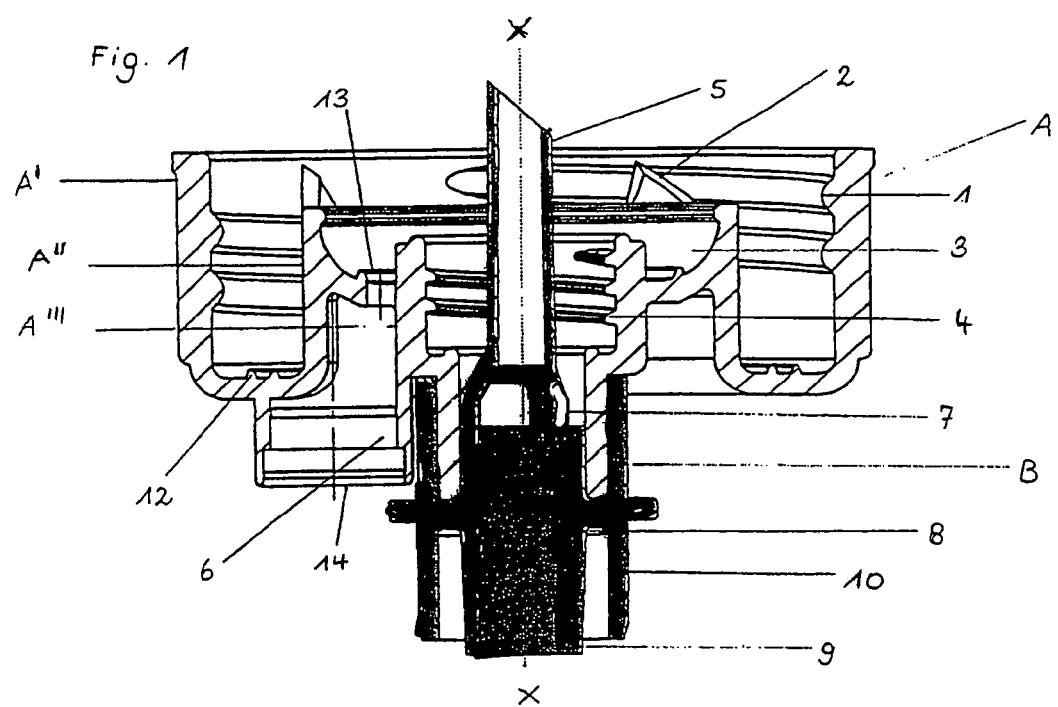
FIG. 1 a one-dimensional longitudinal section through an embodiment of the multipurpose connector in accordance with the invention.

The multipurpose connector shown in FIG. 1 comprises a first part piece A and a second part piece B. The first part piece A includes an outer connector A' having an internal thread 1 for the connection of wide-mouth bottles made of glass or plastic and sealing ribs 12, a middle connector A" having a snap connection 3 for the connection of narrow-mouth bottles and an inner connector A''' as a guide having an internal thread 4 for the connection of bags having puncture ports. An incisor 2 for the opening of cover foils on wide-mouth containers is located at the edge of the middle connector. The second part piece B has a central spike 5 as a distal connector for puncturing in ports. Lateral material cut-outs 7 at the base of the spike avoid the formation of residual liquid. The proximal side of the part piece B is tubular and serves as a drip former 8 on gravity-operated enteral feeding. A tube adhesion point 9 for pump-assisted enteral feeding is located at the end of the drip former 8. The assembly of a drip chamber takes place via the projection 10. All the connectors are arranged coaxially with respect to a common axis X-X.

Starting from the middle distal connector, a venting passage 6 is integrated into the multipurpose connector. An assembly comprising an outwardly disposed valve and a bacteria-tight filter can be inserted therein. The inner venting passage opening 13 is located in the middle distal connector and terminates largely flush with its base. The outer venting passage opening 14 is vertically aligned.

Figure 2:
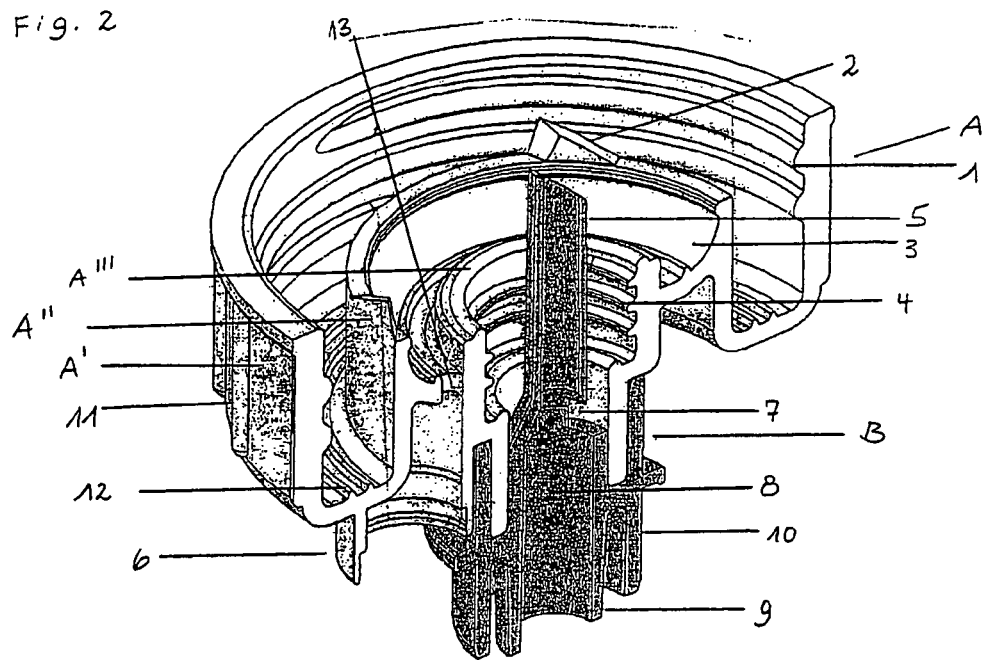
FIG. 2 a three-dimensional longitudinal section through an embodiment of the multipurpose connector in accordance with the invention.
Figure 4A:
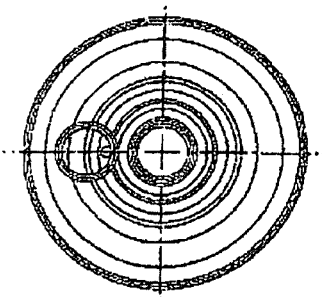
FIGS. 4a-g different views of the first part piece of the multipurpose connector in accordance with the invention.
Figure 4B:
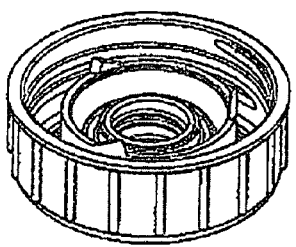
Figure 4C:
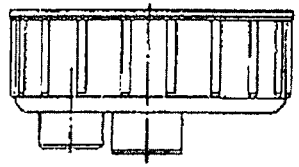
Figure 4D:
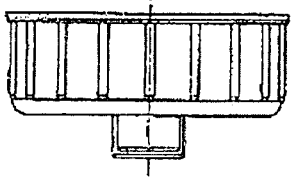
Figure 4G:
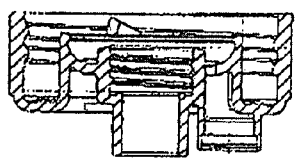
Figure 4E:
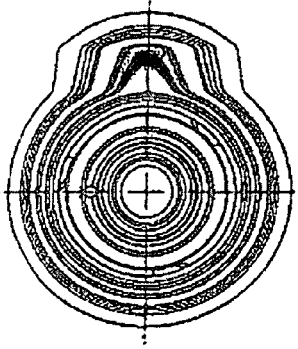
Figure 4F:
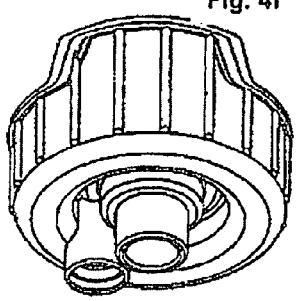

The gripping lugs 11 outwardly attached to the multipurpose container can be seen in FIG. 2.

FIG. 3 shows the multipurpose connector in various views, with 3a representing an outer view, 3b representing a transverse section and 3c representing a longitudinal section with a connected port 15.

In FIGS. 4a-g, different views are shown of the first part piece of the multipurpose connector in accordance with the invention; in FIGS. 5a-f different views of the second part piece.

FIG. 6 shows an alternative of the multipurpose connector as a one-piece embodiment. The venting passage 6 is likewise located in the outer region of the connector.

The inner venting opening 13 is still located in the middle distal connector and terminates largely flush with its base; the outer venting passage opening 14 is, however, aligned horizontally.

After the connection of a storage container by screwing or placing onto one of the connectors, the application medium flows into the transfer system through the multipurpose connector along the line X-X via a drip chamber or a tube. The venting opening 6 ensures an undisturbed outflow.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A multipurpose connector comprising three different distal connectors including an outer distal connector, a middle distal connector and an inner distal connector, said three distal connectors disposed concentrically in one another and coaxially with respect to one another for the connection of enteral transfer systems to storage containers having differently configured openings, each of said three distal connectors including either a threaded or a snap connection, said multipurpose connector having a drip former which defines a fluid channel extending axially through said inner distal connector, said multipurpose connector having two further proximal connectors located on the opposite proximal side of the distal connectors for the storage containers, and a venting passage having an inner vent opening that ends flush with the base of said middle distal connector, said venting passage being a separate opening in the connector from said fluid channel.

2. The multipurpose connector in accordance with claim 1, wherein a tube can be connected to one of the two proximal connectors and a drip chamber can be connected to the other proximal connector.

3. The multipurpose connector in accordance with claim 1, wherein said multipurpose connector includes two pieces.

4. The multipurpose connector in accordance with claim 3, wherein the first piece includes the outer distal connector and the middle distal connector and a part of the inner distal connector and the second piece includes the other part of the inner distal connector and the two proximal connectors.

5. The multipurpose connector in accordance with claim 3, wherein the venting passage is provided in the first piece.

6. The multipurpose connector in accordance with claim 5, wherein a bacteria-tight filter and a valve can be inserted into the venting passage as an outwardly disposed assembly.

7. The multipurpose connector in accordance with claim 5, wherein the inner opening of said venting passage is arranged in the middle distal connector.

8. The multipurpose connector in accordance with claim 1, wherein the first piece is transparent.

9. The multipurpose connector in accordance with claim 1, wherein the outer distal connector is provided with a screw thread.

10. The multipurpose connector in accordance with claim 9, wherein the middle distal connector is made as a snap connection.

11. The multipurpose connector in accordance with claim 10, wherein the inner distal connector includes a guide having a thread and a central spike.

12. The multipurpose connector in accordance with claim 11, wherein the central spike has lateral material cut-outs for the better drainage of liquid.

13. The multipurpose connector in accordance with claim 9, wherein wide-mouth containers can be connected to the outer distal connector.

14. The multipurpose connector in accordance with claim 10, wherein narrow-mouth containers can be connected to the middle distal connector.

15. The multipurpose connector in accordance with claim 11, wherein flexible containers can be connected to the inner distal connector.

16. The multipurpose connector in accordance with claim 1 as part of a set for the connection of nutrient and balancing liquid containers to a feed probe.

17. The multipurpose connector as set forth in claim 1, wherein said venting passage is laterally offset with respect to said fluid channel.

18. The multipurpose connector as set forth in claim 17, wherein said inner vent opening is in fluid communication with an inner venting passage that extends substantially parallel with said fluid channel, said inner venting passage in fluid communication with an outer venting passage that is substantially perpendicular to said inner venting passage.

19. The multipurpose connector as set forth in claim 18, wherein said vent opening of said inner venting passage opens into the central distal connector.

20. The multipurpose connector as set forth in claim 19, wherein said outer venting passage has an outer venting passage opening that is located in an outer part of said connector between said three distal connectors and said two proximal distal connectors.

21. The multipurpose connector as set forth in claim 17, wherein each of said three distal connectors include either a threaded connection or a snap connection.

22. A multipurpose connector comprising three different distal connectors on a distal side including an outer distal connector, a middle distal connector and an inner distal connector, said three distal connectors disposed concentrically in one another and coaxially with respect to one another for the connection of enteral transfer systems to storage containers having differently configured openings, each of said three distal connectors including either a threaded connection or a snap connection, said multipurpose connector having two further proximal connectors located on a proximal side opposite the distal connectors for the storage containers, and a venting passage having an inner vent opening that ends flush with the base of said middle distal connector, said venting passage being a separate opening in the connector from a fluid channel.

* * * * *